United States Patent [19]
Carton

[11] 4,358,685
[45] Nov. 9, 1982

[54] COOLED FILM CASSETTE FOR GAMMA RADIOGRAPHY

[75] Inventor: Jean Carton, Le Bourget, France
[73] Assignee: Alsthom-Altantique, Paris, France
[21] Appl. No.: 194,728
[22] Filed: Oct. 7, 1980
[30] Foreign Application Priority Data
Oct. 10, 1979 [FR] France .................. 79 25192
[51] Int. Cl.³ ............. G01N 23/04; G03B 41/18
[52] U.S. Cl. .............................. 250/475.2; 378/58
[58] Field of Search ..................... 250/475.1, 320
[56] References Cited
U.S. PATENT DOCUMENTS
1,923,108  8/1933  Mehl et al. .................. 250/475.1
4,051,369  9/1977  Takeshita ..................... 250/321

FOREIGN PATENT DOCUMENTS
1172264 10/1958  France .
906406  9/1962  United Kingdom .

Primary Examiner—Alfred E. Smith
Assistant Examiner—T. N. Grigsby
Attorney, Agent, or Firm—Sughrue, Mion, Zinn, Macpeak & Seas

[57] ABSTRACT

A cassette particularly for supporting a gamma radiography film (12). Said cassette comprises a channel section bar (1) with two flanges (3, 4) to which a tube (5, 7) is welded. A cooling fluid is made to flow through said tube. The film needs cooling when hot, recently welded parts are inspected for weld defects.

5 Claims, 5 Drawing Figures

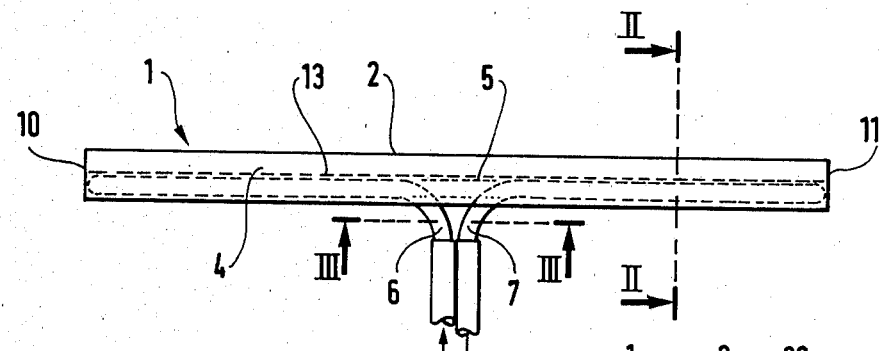
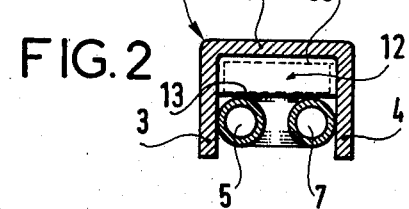
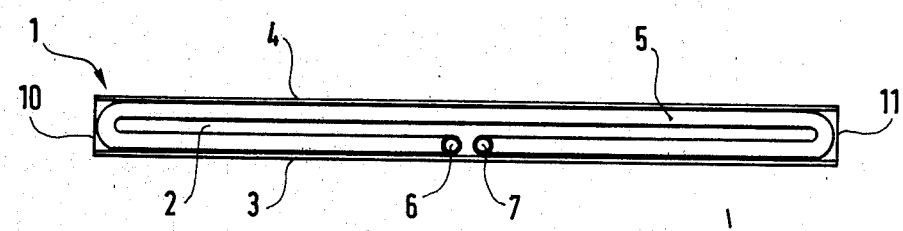
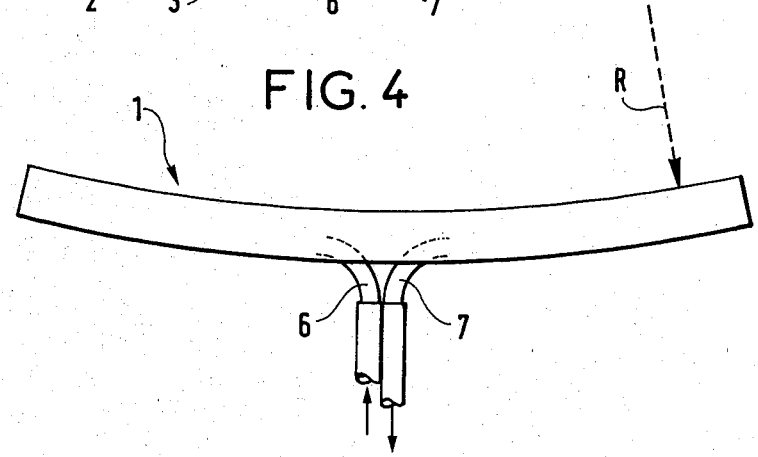

COOLED FILM CASSETTE FOR GAMMA RADIOGRAPHY

The invention relates to a cooled cassette for containing a gamma radiography film designed, for example, to inspect the quality of welds in a turbine shaft.

BACKGROUND TO THE INVENTION

The manufacture of turbine shafts by welding has been known for a long time. It includes the following steps:

the shaft components to be welded are machined so that they interlock while leaving a circular groove in between two adjacent components; these components are then stacked vertically;

the assembly thus formed is heated to a temperature of about 300° C.;

the bottoms of the grooves are welded in several passes, here called bottom passes, and preferably under an argon atmosphere;

the shaft is placed in a horizontal position;

the grooves are filled by several passes of automatic welding; and stress is released by annealing.

The quality of the bottom pass welding is inspected before the filling passes are performed.

This inspection is made by gamma radiography; for that purpose, a radioactive source which emits gamma rays is inserted inside the shaft and held on its axis.

A film which is sensitive to gamma rays is placed in the groove delimited by two adjacent shaft components welded together, and is exposed for a suitable period of time to the gamma radiation which passes through the weld. After development, the film shows up possible defects in the weld such as cracks, failure of the weld to penetrate, etc.

Such quality control by gamma radiography requires the welded parts to be cooled from the temperature of 300° C. to which they are raised, as stated above, to satisfy the requirements of good welding technique. Indeed, a gamma radiography film cannot withstand a temperature of more than 40° C. and the exposure times required to take a photograph range between 15 minutes and 1½ hours depending on the degree of activity of the radioactive source.

Therefore, it is understandable that taking quality control photographs requires parts to be prior cooled from 300° C. to a temperature close to ambient temperature.

Now, it takes several days to cool large parts such as, for example, the shaft of a steam turbine for a 1300 megawatt generator.

If, in extraordinary circumstances, a defective weld is detected, the part must be reheated, the defect repaired, the part cooled and a new photograph taken.

These operations take a considerable time (up to 10 days) during which the welding unit cannot be used. Now, the greater part of the time during which the welding unit is unavailable is taken up by the cooling time and since the cooling time cannot be reduced, techniques have been sought to reduce the time during which the welding unit is unavailable e.g. by performing the gamma radiography while the parts are still at a high temperature.

With this aim in view, film support cassettes have been produced which are cooled to keep the film at a bearable temperature while it is in the neighbourhood of a metal part which is brought down to a temperature of about 200° C. or more.

Previously manufactured cassettes are not satisfactory. In some cases, where they are air-cooled, cooling is insufficient for the application in question. Other cassettes include a layer of water interposed between the film and the source of heat and radiation. Cooling is then sufficient but the quality of the photo is unsatisfactory because the layer of water produces parasitic images on the film.

One aim of the invention is to produce a cassette which does not have the above-mentioned disadvantages.

SUMMARY OF THE INVENTION

The invention therefore provides a gamma radiography cassette comprising: a channel section bar with a web and two flanges and made of a metal which is a good conductor of heat. At least one tube is welded to at least one of said flanges over at least a part of its length thereof parallel to the web for conveying a cooling fluid flowing therethrough, the space lying between the tube and wherein the web being of sufficient size to receive a gamma radiography film.

According to a particular embodiment for inspecting curved objects, the cassette is curved such that the flanges remain in parallel planes while the web occupies a generally curved surface.

Advantageously, the cassette includes a single cooling tube, a first end of which corresponds to the cooling fluid inlet and a second end of which corresponds to the cooling fluid outlet. The ends are disposed substantially in the middle of the cassette with the tube extending along the flanges of the cassette and being bent back in a U-shaped configuration at each end of the cassette.

Preferably, the bar is made of a metal chosen from among copper and brass.

Advantageously, the thickness of the bar lies between 3 and 10 tenths of a millimeter, thereby ensuring adequate heat conduction without degrading the quality of the image.

BRIEF DESCRIPTION OF THE DRAWINGS

The invention will be better understood from the description given below of a single embodiment with reference to the accompanying drawings in which:

FIG. 1 is an elevation of a cassette in accordance with one embodiment.

FIG. 2 is an enlarged view showing a cross-section along line II—II in FIG. 1.

FIG. 3 is a cross-section view along line III—III in FIG. 1.

FIG. 4 is an elevation of a cassette with a curved web.

DETAILED DESCRIPTION

Figure 5:
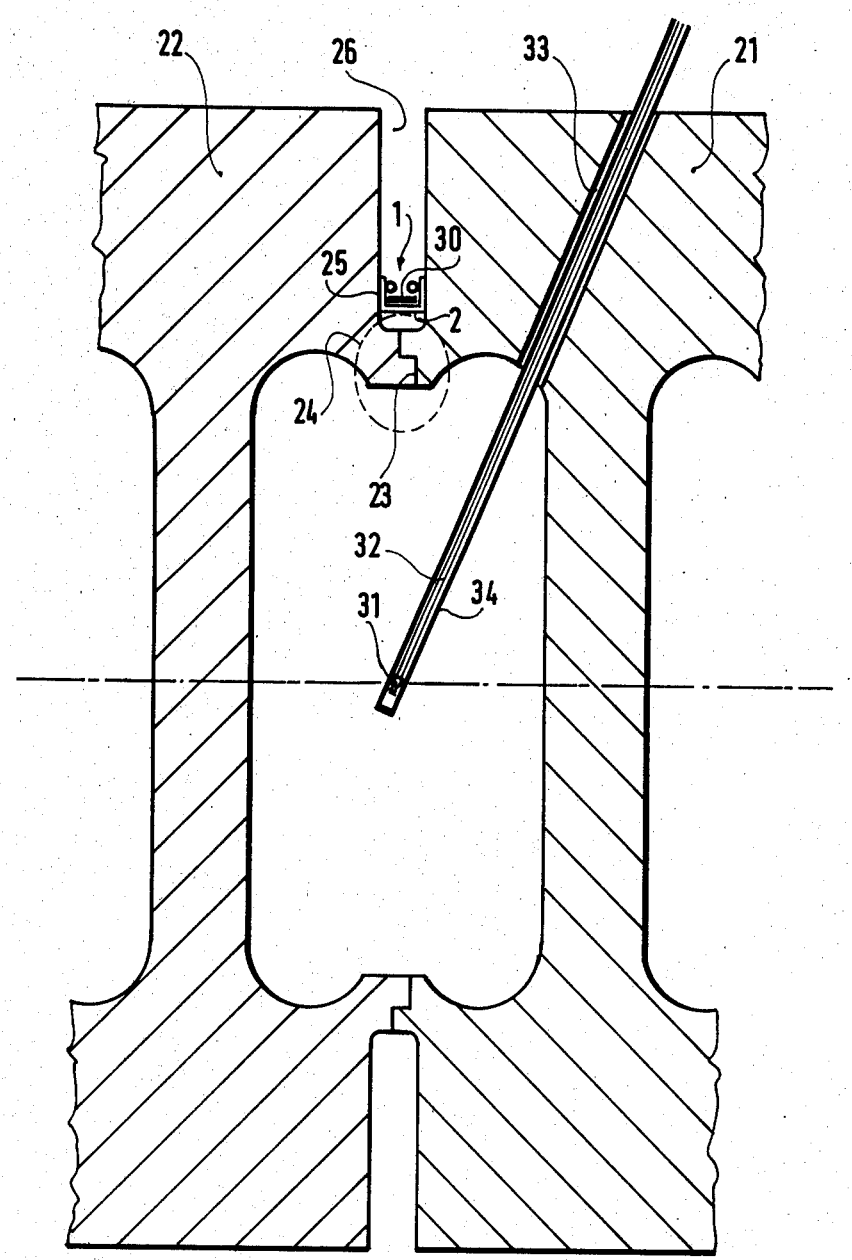
FIG. 5 is a sectional view which shows an example of application of the film container cassette to gamma radiography of a turbine shaft weld.

FIGS. 1, 2 and 3 illustrate a cassette in accordance with a first embodiment of the present invention. Said cassette is designed to contain films and includes essentially a channel section bar 1 with a web 2 and flanges 3 and 4. Said bar is made of a metal (copper or brass) which is a good conductor of heat and whose thickness lies between 3 and 10 tenths of a millimeter.

The edges of a copper or brass tube 5 are welded to the inside of the flanges of the bar. The inlet 6 and the outlet 7 of the tube are located substantially at the center of the bar. The tube near inlet 6 is welded to a first half of the flange 3 of the bar, is bent round at one end 10, is welded to the opposite flange along its entire length, is bent round at the other end 11 of the bar and is welded near outlet 7 to the remaining half of the flange 3. A thin strip 13 of copper or brass is disposed between the tube 5 and the web 2 to form a housing for the film.

The inlet of the tube is connected to a source (not shown) of cooling fluid which can simply be water at ambient temperature (about 20° C.) at normal water mains distribution pressure.

The space 12 delimited by the web 2, the flanges 3 and 4 and the strip 13 (FIG. 2) allows a gamma radiography film 30 fitted with reinforcing screens to be inserted therein. The web 2 which, in use, lies in between the weld to be radiographed and the film, does not constitute an obstacle for gamma rays but, on the contrary, performs the function of a reinforcing member known to gamma radiography technicians. Once the film has been inserted in its housing, the ends of the housing can be closed to light by means of suitable end stoppers (not shown).

To radiograph the welds of turbine shafts, a degree of curvature of radius R can be imparted to the web 2 as shown in FIG. 4.

By way of example, it is possible to provide a cassette 820 mm long capable of holding two 400-mm films and having a radius of curvature of 730 mm.

FIG. 5 shows an example of application to gamma radiography of two shaft components 21 and 22 welded along their line of contact 23. The zone 24 which is surrounded with a circle in dashed lines is completely recast after the bottom passes (as herein before defined). The gamma radiography cassette 25 is disposed in the slot 26 formed by the shaft components and its web 2 is turned towards the bottom of the slot. Gamma radiography film 30 is shown in FIG. 5.

Said film is subjected to the radiation of a radioactive source 31 held in the center of the shaft at the end of a flexible tube 32 enclosed in a tube 34 which is inserted through a cavity 33 formed in the shaft component 21.

Applications are found for cassettes in accordance with the invention in any case where it is required to make a gamma radiograph of a weld without waiting for the parts to cool (welding boilers, large boiler ware components, etc.).

Due to the good heat conduction of all the component parts of a cassette in accordance with the invention, the film is well cooled since it is possible to radiograph parts at 200° C. or more without danger. Parts have even been radiographed at 280° C. without damage to the film. The compactness of the cassette suits it to any application, particularly to inspecting welds at the bottoms of slots. It can easily be fixed by any means on the parts to be inspected. It provides complete support means for the film and, provided a film-supporting strip such as the strip 13 is used together with end stoppers, the cassette can be arranged to keep the film in the dark out of reach of light.

I claim:

1. A cooled film cassette for gamma radiography, the cassette comprising: a channel section bar including a web joining two flanges, said bar being made of a metal which is a good conductor of heat; and at least one tube welded to at least one of said flanges over at least a part of its length parallel to the web for conveying a cooling fluid flowing therethrough, and said tube being spaced from said bar web and forming a space lying between the tube and the web of sufficient size to carry a gamma radiography film.

2. A cassette according to claim 1, wherein the cassette is curved such that the flanges remain in parallel planes while the web occupies a generally curved surface.

3. A cassette according to claim 1, wherein the bar is made of a metal chosen from the group consisting of copper and brass.

4. A cassette according to claim 3, wherein the thickness of the bar lies between 3 and 10 tenths of a millimeter.

5. A cassette according to any previous claim, wherein the cassette includes a single cooling tube, a first end of which forms the cooling fluid inlet and a second end which forms the cooling fluid outlet, said ends being disposed substantially in the middle of the cassette, the tube including parallel portions extending along the flanges of the cassette in opposite directions from the center of the bar and being bent back in a U-shaped configuration at each end of the cassette.

* * * * *